(12) United States Patent
Bonomo et al.

(10) Patent No.: US 8,575,346 B2
(45) Date of Patent: Nov. 5, 2013

(54) RUTHENIUM BASED COMPLEXES

(75) Inventors: Lucia Bonomo, Geneva (CH); Philippe Dupau, Geneva (CH); Serge Bonnaudet, Geneva (CH)

(73) Assignee: Firmenich SA, Geneva (CH)

( * ) Notice: Subject to any disclaimer, the term of this patent is extended or adjusted under 35 U.S.C. 154(b) by 0 days.

(21) Appl. No.: 13/698,508

(22) PCT Filed: Jun. 1, 2011

(86) PCT No.: PCT/IB2011/052410
§ 371 (c)(1),
(2), (4) Date: Nov. 16, 2012

(87) PCT Pub. No.: WO2011/161570
PCT Pub. Date: Dec. 29, 2011

(65) Prior Publication Data
US 2013/0060035 A1    Mar. 7, 2013

(30) Foreign Application Priority Data
Jun. 22, 2010  (EP) .................... 10166820

(51) Int. Cl.
C07D 15/00    (2006.01)
C07D 213/79   (2006.01)
C07D 17/02    (2006.01)

(52) U.S. Cl.
USPC .................... 546/5; 546/4; 556/136

(58) Field of Classification Search
CPC ........ C07F 15/00; C07F 17/02; C07D 213/79
See application file for complete search history.

(56) References Cited

PUBLICATIONS

Johnstone, RA. et al. Heterogeneous Catalytic Transfer Hydrogenation and Its Relation to Other Methods for Reduction of Organic Compounds. Chem. Rev. 1985, vol. 85, p. 141, C1.*
Dorwold, FZ. Side Reactions in Organic Synthesis. Wiley. 2005, preface.*
International Search Report and Written Opinion of the International Searching Authority, application No. PCT/IB2011/052410, mailed Jan. 11, 2012.
Albers et al., "Dinuclear Ruthenium (II) Carboxylate Complexes," Inorganic Syntheses, 26:249-258 (Nov. 1989).
Albers et al., "Dimeric ruthenium(II) complexes containing bridging carboxylato and aquo ligands. The crystal structure of (β-aquobis(μ-trifluoroacetato)bis[($\eta^4$-cycloocta-1,5-diene)(trifluoroacetato)ruthenium(II)]," Journal of Organometallic Chemistry, 272(3):C62-C66 (Sep. 1984).
Demerseman et al., Direct Preparation of [Ru($\eta^2$-O$_2$CO)($\eta^6$-arene)(L)] Carbonate Complexes (L = Phosphane, Carbene) and Their use as Precursors of [RuH$_2$(p-cymene)(PCy$_3$)] and [Ru($\eta^6$-arene)(L)(MeCN)$_2$][BF$_4$]$_2$: X-ray Crystal Structure Determination of [Ru($\eta^2$-O$_2$CO)(p-cymene)(PCy$_3$)] 1/2CH$_2$Cl$_2$ and [Ru($\eta^2$-O$_2$-CO)($\eta^6$C$_6$Me$_6$)-(PMe$_3$)] $_{H_2}$O, European Journal Inorganic Chemistry, 2006(6):1174-1181 (Mar. 2006).
Doucet et al., "Enantioselective Hydrogenation of 2'-Chloroacetophenone with ((R)-Binap)Ru(O$_2$CAr)$_2$ complexes : Influence of Carboxylate Ligands and Solvents," Tetrahedron: Asymmetry, 7(2):525-528 (Feb. 1996).
Heiser et al., "New Efficient Methods for the Synthesis and In-Situ Preparation of Ruthenium(II) Complexes of Atropisomeric Diphosphines and Their Application in Asymmetric Catalytic Hydrogenations," Tetrahedron: Asymmetry, 2(1):51-62 (1991).
Noyori et al., "Asymmetric Synthesis of Isoquinoline Alkaloids by Homogeneous Catalysis," J. Am. Chem. Soc., 108(22):7117-7119 (Oct. 1986).
Ohta et al., "Asymmetric Hydrogenation of Unsaturated Carboxylic Acids Catalyzed by BINAP-Ruthenium(II) Complexes," J. Org. Chem., 52(14):3174-3176 (Jul. 1987).
Takaya et al., "Enantioselective Hydrogenation of Allylic and Homoallylic Alcohols," J. Am. Chem. Soc., 109(5):1596-1597 (Mar. 1987).

* cited by examiner

*Primary Examiner* — Rita Desai
*Assistant Examiner* — Ben S Michelson
(74) *Attorney, Agent, or Firm* — Winston & Strawn LLP

(57) ABSTRACT

The present invention relates to the field of catalysis and, more particularly, to a ruthenium carbonate complex of formula [Ru(diene)(C0$_3$)] or [Ru(diene)(C0$_3$)$_2$]M$_n$, wherein M is an alkaline (n is 2) or alkaline earth (n is 1) cation. The invention relates also to the use of said ruthenium carbonate complex as precursors for a number of Ru carboxylate complexes. Said specific ruthenium complexes possess a number of important advantages over the similar prior art known precursors.

12 Claims, No Drawings

RUTHENIUM BASED COMPLEXES

TECHNICAL FIELD

The present invention relates to the field of catalysis and, more particularly, to a specific type of ruthenium carbonate complexes, as well as their preparation, as useful precursors for a number of Ru carboxylate complexes. Said specific ruthenium complexes possess a number of important advantages over the similar prior art known precursors.

PRIOR ART

Some ruthenium carboxylate complexes of general formula [Ru(diene)(OOCR)$_2$]$_n$, with n equal to 1 or 2, have been described as useful starting compounds for the preparation of a number of ruthenium-diphosphine (PP) complexes of formula [Ru(PP)(OOCR)$_2$], which are good catalysts for the hydrogenation of carbon-carbon double bonds (e.g. see. O. Albers et al. *J. Organomet. Chem*, 1984, C62, 272; Ohta T. et al. in *J. Org. Chem.*, 1987, 52, 3174-3176; Noyori R. et al. in *J. Am. Chem. Soc.*, 1986, 108, 7117-7119; or Takaya H. et al. in *Am. Chem. Soc.*, 1987, 109, 1596-1597).

Despite their usefulness, only indirect synthesis (i.e. more than one step) of said [Ru(diene)(OOCR)$_2$]$_n$ from [(diene) RuCl$_2$]$_n$ (which is one of the most common commercially available starting materials) is described in the literature. Indeed, the reported preparations of [Ru(diene)(OOCR)$_2$]$_n$ require as intermediates of type [(diene)Ru(methylallyl)$_2$], as shown in the following scheme:

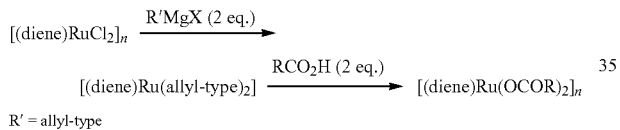

R' = allyl-type

This way, the preparation of some complexes of type [(diene)Ru(OOCR)$_2$]$_n$, wherein diene is COD or NBD, and R is CF$_3$, CCl$_3$, CHCl$_2$, CH$_3$ or some aryl, has been described (see H. Doucet et al., *Tetrahedron Asymmetry*, 1996, 7, 525-528; B. Heiser et al., *Tetrahedron Asymmetry*, 1991, 2(1), 51-62; M. O. Albers et al., *Inorganic Syntheses*, 1989, 26, 249-58; or M. O. Albers et al. *J. Organomet. Chem*, 1984, C62, 272).

The synthetic pathway described in those publications suffers from the following major drawbacks:
- the synthesis of the allyl intermediates, such as [(diene)Ru (bismethylallyl)$_2$], obtained from [Ru(diene)Cl$_2$]$_n$, is very diluted and requires the use of a Grignard reagent and the intermediates obtained are only mildly stable, in both solution and solid state, thus complicating an industrial implementation of such synthetic operations;
- the preparation of [Ru(diene)(OOCR)$_2$]$_n$ with the prior art method requires at least two steps starting from [Ru(diene)Cl$_2$], and requires the formation of an intermediate difficult to handle;
- methylallyl ligand displacement by protonation is shown only using halo acetic acids or some aryl carboxylic acids, i.e this method is not general;
- [(COD)Ru(acetate)$_2$] could not be obtained directly from the bis-methylallyl complex and had been synthesized from [(COD)Ru(OOCCF$_3$)$_2$]$_2$ by anionic ligand exchange with acetate salts, adding thus an additional step to the overall process. Moreover the overall yield of its preparation is quite poor.

Therefore there is a need for an improved process for obtaining complexes of type [(diene)Ru(OOCR)$_2$]$_n$, wherein the intermediates of type [(diene)Ru(bismethylallyl)$_2$] are not required.

DESCRIPTION OF THE INVENTION

We have now surprisingly found that the complexes [(diene)Ru(OOCR)$_2$]$_n$ can be directly obtained, in one step, from a new precursor, in the form of a Ru carbonate complex, by reacting said precursor with a carboxylic acid under specific convenient and highly productive reaction conditions.

In order to overcome the problems aforementioned, the present invention relates to a process for the preparation of a compound of formula $$\{[(\text{diene})\text{Ru}(\text{OOCR}^1)_2]_n(\text{H}_2\text{O})_v\} \qquad (I)$$

wherein n is 1 or 2;
v is 0 or 1;
"diene" represents a linear or branched C$_4$-C$_{15}$ hydrocarbon compound comprising two carbon-carbon double bonds or a cyclic C$_7$-C$_{20}$ hydrocarbon group comprising two carbon-carbon double bonds; and
R$^1$ represents:
  a hydrogen atom;
  a pyridyl group;
  a phenyl group optionally substituted by one to five halogen atoms and/or C$_{1-4}$ alkyl or alkoxyl groups; or
  a C$_{1-18}$ alkyl or alkenyl, optionally halogenated, and optionally comprising:
    one or two phenyl group, each phenyl group being optionally substituted by one to five halogen atoms and/or by C$_{1-4}$ alkyl or alkoxyl groups; and/or
    one or two OH, amino, ether or thioether functional groups;
comprising the step of reacting a precursor compound of the formulae

[Ru(diene)(CO$_3$)$_2$]M$_n$ or   (II)

[Ru(diene)(CO$_3$)]   (II')

wherein "diene" has the same meaning as defined in formula (I), M is an alkaline (n is 2) or alkaline earth (n is 1) cation;
in the presence of a carboxylic acid R$^1$COOH, wherein R$^1$ is as defined above.

For the sake of clarity, by the expression "halogenated" it is meant that said group may be perhalogenated, i.e. all hydrogen atoms are replaced by halogen atoms, or partially halogenated, in particular may comprise from one to 5 halogen atoms such as Cl or F.

For the sake of clarity, it has to be mentioned that compound (I) comprises complexes having various structures, that is to say monomers wherein each R$^1$COO group is coordinated to only one Ru (i.e. [(diene)Ru(OOCR$^1$)$_2$]), or dimers wherein at least one of the R$^1$COO groups is coordinated to two Ru (e.g. [(diene)Ru(OOCR$^1$)(μ-OOCR$^1$)]$_2$ or [((diene) Ru(μ-OOCR$^1$)$_2$]$_2$).

For the sake of clarity, it has to be mentioned that by the expression "hydrocarbon compound comprising two carbon-carbon double bonds", used in the definition of diene, it is meant a neutral ligand and not an allylic ligand.

According to a particular embodiment of the invention, said "diene" is a $C_7$-$C_{12}$, or a $C_7$-$C_{10}$, hydrocarbon compound comprising two carbon-carbon double bonds, optionally substituted, e.g. a cyclic $C_7$-$C_{12}$, or a $C_7$-$C_{10}$, hydrocarbon compound comprising two carbon-carbon double bonds. As well understood by a person skilled in the art, by "cyclic hydrocarbon" it is understood a compound comprising a cyclic moiety.

As non-limiting examples of suitable "diene" one may cite compounds such as COD (cycloocta-1,5-diene) or NBD (norbornadiene), 2,4-dimethyl-1,3-pentadiene or yet cyclohepta-1,4-diene.

The examples of "diene" provided above are applicable for both compounds (I) and (II). Anyhow, as a person skilled in the art would recognise, the diene present in the precursor (II) will be the same as the one of the compound (I) obtained by the present invention.

Another constituent of compound (I) is the carboxylic group $R^1COO$. The compounds of formula (I) can be monomeric (n=1), or dimeric (n=2) depending mainly on the exact nature of the group $R^1$, e.g. when $R^1$ is a methyl group the compound is monomeric while when $R^1$ is $CCl_3$ the compound is dimeric. In some cases said compound (I) may exist in the two forms (monomeric and dimeric).

According to a particular embodiment of the invention, said $R^1$ group represents:
- a $C_{1-12}$ alkyl group, optionally halogenated, and optionally comprising:
  - one phenyl group optionally substituted by one to five halogen atoms and/or by $C_{1-4}$ alkyl or alkoxyl groups; and/or
  - one OH, amino or ether functional group;
  or
- a phenyl group optionally substituted by one to five halogen atoms and/or by $C_{1-4}$ alkyl or alkoxyl groups.

According to a particular embodiment of the invention, said $R^1$ represents a $C_{2-10}$ alkyl group, optionally branched in the α and/or β position.

According to another particular embodiment of the invention, said $R^1$ is a group $R^2$ representing a branched $C_{2-10}$ alkyl group comprising in the α position a tertiary or quaternary carbon atom and/or in the β position a quaternary carbon atom and said $R^2$ optionally comprising one OH, amino or ether functional group, and also optionally comprising one phenyl group, the phenyl group being optionally substituted by one to five halogen atoms and/or by $C_{1-4}$ alkyl or alkoxyl groups.

For the sake of clarity, by the expression "α position" it is meant the usual meaning in the art, i.e. the carbon atom directly bound to the COO moiety of the group $R^2COO$. Similarly by the expression "β position" it is meant a carbon atom directly bound to the α position.

According to a particular embodiment of the invention, the optional substituents of the phenyl group in the above embodiments are one, two or three halogen atoms, such as Cl and/or F, and/or $C_{1-4}$ alkyl or alkoxyl groups.

The examples of group $R^1$ provided above are applicable for both compound (I) and compound $R^1COOH$. Anyhow, as a person skilled in the art would recognise, the group $R^1$ present in compound $R^1COOH$ will be the same as the one of the compound (I) obtained by the present invention. The same applies to the group $R^2$, in which case the carboxylic acid will be of formula group $R^2COOH$.

As non-limiting examples of suitable $R^1COOH$, or $R^2COOH$, and consequently of the $R^1COO$ group of (I), or respectively $R^2COO$, one may cite the following acids: acetic, the mono-, di-, tri-chloroacetic, propionic, isobutyric, pivalic, $^tBu$-acetic, 2-Et-hexanoic, cyclohexanecarboxylic, picolinic, cinnaminic, benzoic, 4-Me-benzoic, 4-OMe-benzoic, 3,5-dichloro-benzoic, isovaleric, 1-adamantanecarboxylic or sec-butyric acid.

The process of the invention is advantageously carried out in the presence of a solvent, especially in the case where the compound $R^1COOH$ is not itself a liquid which could be used as diluent of the medium. It is also well understood by the person skilled in the art that said solvent is a liquid with a melting point below the reaction temperature. In the present invention, the exact nature of the solvent is not a critical element; however, as a person skilled in the art known, the choice of the solvent can be influenced by practical consideration such as the selective solubility of only one of the invention's process products (e.g. the compound of formula (I) or the salts formed such as $R^1COOM$, if M is an alkaline cation).

According to a particular embodiment of the invention, as typical examples of said solvent one may cite the following ones:
- water;
- $C_{1-5}$ alcohols, in particular methanol, ethanol, propanol or iso-propanol;
- $C_{4-8}$ ethers, in particular tetrahydrofurane, methyl ter-butyl ether or dibutyl ether;
- $C_{6-9}$ derivatives of benzene, in particular toluene, xylene, anisol or p-cymene;
- $C_{3-9}$ esters, in particular methyl, ethyl, isopropyl or butyl acetate; and
- mixtures thereof.

Particularly appreciated solvents are water, $C_{1-3}$ alcohols such as methanol, $C_{4-6}$ ethers such as tetrahydrofurane or mixtures thereof.

The process of the invention as mentioned can be carried out in a broad range of temperature. According to a particular embodiment of the invention, the temperature is comprised between 10° C. and 100° C., more preferably between 20° C. and 70° C. Of course, a person skilled in the art is also able to select the preferred temperature as a function of the melting and boiling point as well as of the specific properties of said solvent as well as the desired time of reaction or conversion.

The process of the invention can be carried out under an inert or an oxygen containing atmosphere. As a person skilled in the art knows, the exact nature of the atmosphere depends on many factors such as the stability of products used or generated during the process towards oxygen. According to an embodiment of the present invention, it is preferable to carry out the process under an inert atmosphere (such as a nitrogen or argon atmosphere). However in many cases, for example when it is used a carboxylic acid of formula $R^2COOH$, the nature of the atmosphere is indifferent, for instance it can be used an inert atmosphere, or an oxygen containing atmosphere (e.g. any mixture of an inert atmosphere and oxygen, such as for example air).

Typical manners to execute the invention's process are reported herein below in the examples.

The precursor (II) or (II') is a novel compound and presents a number of advantages. Indeed this compound (II) or (II'), to the contrary of the prior art as [(diene)Ru(bismethylallyl)$_2$], is very stable towards hydrolysis and oxygen, as well as a number of other parameters. Compound (II) or (II') is also more reactive compared to [(diene)Ru(bismethylallyl)$_2$], in particular towards aliphatic carboxylic acids, allowing then direct preparation of a greater diversity of compounds [Ru(diene)(OOCR)$_2$]$_n$. Therefore its use in the above described process allows to solve many of the drawbacks mentioned about the prior art process to produce [Ru(diene)(OOCR)$_2$]$_n$ complexes.

Therefore, another object of the present invention concerns the compounds of formula $$[Ru(diene)(CO_3)_2]M_n \text{ or} \quad (II)$$

$$[Ru(diene)(CO_3)] \quad (II')$$

wherein "diene" has the same meaning as defined in formula (I), M is an alkaline (n is 2) or alkaline earth (n is 1) cation.

According to a particular embodiment of the invention, M represents a sodium, potassium, cesium, calcium, stronzium or barium cation. In particular M is a sodium, potassium or cesium cation.

According to a particular embodiment of the compound (II), said compound is $[Ru(COD)(CO_3)_2]Na_2$; $[Ru(COD)(CO_3)_2]K_2$; $[Ru(COD)(CO_3)_2]Cs_2$; $[Ru(NBD)(CO_3)_2]Na_2$; $[Ru(NBD)(CO_3)_2]K_2$ or $[Ru(NBD)(CO_3)_2]Cs_2$ or $[Ru(COD)(CO_3)]$.

It is also understood that the compounds of formula (II) can be in a solvated form, i.e. comprising a solvent coming from the reaction medium of their preparation, or as a mixed co-precipitated salt, i.e. comprising other salts which are obtained by product of their synthesis. This is a standard knowledge of the person skilled in the art and is well exemplified in the examples herein below.

Said compound (II) or (II') can be obtained by reacting $[Ru(diene)(Cl)_2]$ with a suitable alkaline or alkaline earth carbonate, in a suitable solvent such as a polar aprotic solvent and under an inert atmosphere, such as one defined in the above embodiments. The exact nature of the compound obtained (i.e. (II) or (II')) is depending on the molar ratio between the $[Ru(diene)(Cl)_2]$ and the carbonate.

As well understood by a person skilled in the art, by "polar aprotic solvent" it is understood that said solvent has a $pK_a$ above 18 and a dielectric constant ∈ above 20, said constant being measured at standard conditions. Said constants can be retrieved in chemical Handbooks such as "Handbook of Chemistry and Physics", 87$^{th}$ edition, 2006-2007, page 15-13 to 15-23, ISBN 978-0-8493-0487-3, or such as March's "Advanced Organic Chemistry" 5$^{th}$ edition, ISBN 0-471-58589-0, or any other similar reference.

It is also well understood by the person skilled in the art that said solvent is a liquid with a melting point below the reaction temperature. It is also useful to mention that another advantage of the invention's process is that the solvent used does not need particular requirements concerning the water contents, e.g. does not need to be anhydrous, fact that simplifies significantly any industrialisation of said process. In particular a technical grade solvent can be used, e.g. which may contain up to 1 or 2% w/w water.

As typical example of said solvent, one may cite solvents such as $C_{2-12}$ amides, in particular $C_{3-8}$ N-alkyl or N,N-dialkyl amides (e.g. acetamide, N,N-dimethyl-acetamide, N,N-dimethyl-formamide, N-acetyl piperidine or N-acetylpyrrolidine); $C_{6-9}$ N-alkyl lactame (e.g. N-methylpyrrolidone); $C_{4-8}$ carbamates or ureas (e.g. tetramethylurea); or mixtures thereof.

Particularly appreciated solvents are $C_{3-8}$ N,N-dialkyl amides (N,N-dimethyl-formamide or N,N-dimethyl-acetamide), or $C_{5-10}$ lactams (N-methylpyrrolidone).

The process for the preparation of compound (II) or (II') can be carried out in a broad range of temperature. According to a particular embodiment of the invention, the temperature is comprised between 10° C. and 100° C., more preferably between 20° C. and 70° C. Of course, a person skilled in the art is also able to select the preferred temperature as a function of the melting and boiling point, as well as of the specific properties of said solvent, and of the desired time of reaction or conversion.

Typical manners to execute the invention's process are reported herein below in the examples.

EXAMPLES

The invention will now be described in further detail by way of the following examples, wherein the temperatures are indicated in degrees centigrade and the abbreviations have the usual meaning in the art.

All reagents and solvents were used as purchased in technical grade without further purification. NMR spectra were recorded on a Bruker AM-400 ($^1$H at 400.1 MHz, $^{13}$C at 100.6 MHz, and $^{31}$P at 161.9 MHz) spectrometer and normally measured at 300 K, in $CD_2Cl_2$ unless indicated otherwise. Chemical shifts are listed in ppm, and coupling constant in Hz. IR spectra were recorded on a Perkin Elmer FT-IR spectrometer, and the frequencies are given in cm$^{-1}$.

Example 1

Preparation of Complexes $[(diene)Ru(CO_3)_2]M_2$

Synthesis of $\{[(COD)Ru(CO_3)_2][Na]_2\}2(NaCl)$ by Direct Reaction of Polymeric $[(COD)RuCl_2]_n$ with $Na_2CO_3$ Sodium carbonate (189 g, 1.79 mol) was added at room temperature to a suspension of $[(COD)RuCl_2]_n$ (200.0 g, 0.71 mol) in DMF (800 g). The reaction mixture was stirred at 40° C. for 20 hours during which time a solid precipitated out. The reaction mixture was then cooled down to room temperature and the solid formed was collected by filtration. The solid was washed with DMF (100 ml), with $Et_2O$ (200 ml) and dried under vacuum (305 g, yield=87%).

IR (neat) ν: 3000-2800 (w); 1538 (s); 1321 (s).

$^1$H-NMR ($D_2O$): 4.3 (m, 2H, CH); 2.9 (m, 2H, CH); 2.4 (m, 2H, $CH_2$); 2.2 (m, 4H, $CH_2$); 2.0 (m, 2H, $CH_2$).

$^{13}$C-NMR ($D_2O$): 170.6 (O—COO); 88.4 (CH); 86.6 (CH); 34.5 ($CH_2$); 28.9 ($CH_2$).

Synthesis of $[(COD)Ru(CO_3)_2][Cs]_2$: by Direct Reaction of Polymeric $[(COD)RuCl_2]_n$ with $Cs_2CO_3$ Cesium carbonate (29 g, 89 mmol) was added at room temperature to a suspension of $[(COD)RuCl_2]_n$ (10.0 g, 35.6 mmol) in DMF (40 g). The reaction mixture was stirred at 40° C. for 20 hours during which time a solid precipitated out. The reaction mixture was then cooled down to room temperature and the solid formed was collected by filtration. The precipitate was then extracted with MeOH in order to remove salts (such as the CsCl). The solution was evaporated to dryness and the residue was triturated with $Et_2O$ (20 ml) to give a solid recovered by filtration and dried under vacuum (19 g, yield=90%).

IR (neat) ν: 3000-2800 (w); 1560 (s); 1270 (s).

$^1$H-NMR ($D_2O$): 4.3 (m, 2H, CH); 2.9 (m, 2H, CH); 2.4 (m, 2H, $CH_2$); 2.2 (m, 4H, $CH_2$); 2.0 (m, 2H, $CH_2$).

$^{13}$C-NMR (D$_2$O): 170.7 (O—COO); 88.4 (CH); 86.6 (CH); 34.5 (CH$_2$); 28.9 (CH$_2$).

Synthesis of {[(NBD)Ru(CO$_3$)$_2$][Na]$_2$}2(NaCl) by Direct Reaction of Polymeric [(NBD)RuCl$_2$]$_n$ with Na$_2$CO$_3$ Sodium carbonate (5.0 g, 47.3 mmol) was added at room temperature to a suspension of [(NBD)RuCl$_2$]$_n$ (5.0 g, 18.9 mmol) in DMF (20 g). The reaction mixture was stirred at 40° C. for 20 hours during which time a solid precipitated out. The reaction mixture was then cooled down to room temperature and the solid formed was collected by filtration. The solid was washed with DMF (100 ml), with Et$_2$O (200 ml) and dried under vacuum (7.2 g, yield=80%).

IR (neat) ν: 3000-2850 (w); 1577 (s); 1334 (s).

$^1$H-NMR (D$_2$O): 4.54 (br. signal, 2H, CH); 3.90 (br. signal, 2H, CH); 3.69 (br. signal, 2H, CH$_2$); 1.59 (m, 2H, CH).

$^{13}$C-NMR (D$_2$O): 178 (O—COO); 68.4 (CH); 65.1 (CH); 61.0 (CH$_2$); 52.9 (CH).

Synthesis of {[(COD)Ru(CO$_3$)}.(DMF) by Direct Reaction of Polymeric [(COD)RuCl$_2$]$_n$ with Na$_2$CO$_3$ Sodium carbonate (117 g, 1.1 mol) was added at room temperature to a suspension of [(COD)RuCl$_2$]$_n$ (200.0 g, 0.71 mol) in DMF (800 g). The reaction mixture was stirred at 40° C. for 24 hours during which time a solid precipitated out. The reaction mixture was then cooled down to room temperature and the solid formed was collected by filtration. The solid was washed several times with water in order to eliminate salts, with DMF (1×100 ml), with Et$_2$O (2×100 ml) and dried under vacuum (185 g, yield=70%).

Anal. Calcd for {[(COD)Ru(CO$_3$)}.(DMF), C$_{12}$H$_{19}$N$_1$O$_4$Ru: C, 42.10; H, 5.55; N, 4.09; Ru, 29.5. Found: C, 41.5; H, 5.85; N, 4.63; Ru, 28.9.

IR (neat) ν: 3000-2800 (w); 1665 (s); 1546 (s); 1299 (s).

Example 2

Preparation of complexes [Ru(diene)(OOCR)$_2$]$_n$ from the invention's carbonates Synthesis of {[(COD)Ru(O$_2$C$^t$Bu)]$_2$(μ-O$_2$C$^t$Bu)$_2$}: by Direct Reaction of {[(COD)Ru(CO$_3$)$_2$][Na]$_2$}2 (NaCl) with Pivalic Acid in Water Under Nitrogen Pivalic acid (8.7 g, 85 mmol) was slowly added at room temperature to a solution of {[(COD)Ru(CO$_3$)$_2$][Na]$_2$}2(NaCl) (10.0 g, 20.3 mmol) in water (40 g), under nitrogen. A yellow solid precipitated out which was washed with water (10 ml), with MeOH (10 ml) and dried under vacuum (6.0 g; yield=72%).

IR (neat): 2953.5 (m), 2950-2920 (w) 1568.1 (s); 1479 (s), 1406 (s).

$^1$H-NMR: 4.5 (m, 1H, CH); 4.3 (m, 1H, CH); 4.2 (m, 1H, CH); 4.0 (m, 1H, CH); 2.5 (m, 2H, CH$_2$); 2.3 (m, 2H, CH$_2$); 2.2 (m, 1H, CH$_2$); 2.1 (m, 1H, CH$_2$); 2.0 (m, 2H, CH$_2$); 1.12 (s, 9H, tBu); 1.11 (s, 9H, tBu).

$^{13}$C-NMR: 194.5 (O—C=O); 191.9 (O—C=O); 97.9 (CH); 96.5 (CH); 88.5 (CH); 83.5 (CH); 41.6 (C); 40.9 (C); 30.3 (CH$_2$); 29.8 (CH$_2$); 28.4 (CH$_2$); 28.2 (CH$_3$); 28.1 (CH$_2$); 27.9 (CH$_3$).

Synthesis of {[(COD)Ru(O$_2$C$^t$Bu)]$_2$(μ-O$_2$C$^t$Bu)$_2$}: by Direct Reaction of {[(COD)Ru(CO$_3$)$_2$][Na]$_2$}2 (NaCl) with Pivalic Acid in Water Under Air Pivalic acid (8.7 g, 85 mmol) was slowly added at room temperature to a solution of {[(COD)Ru(CO$_3$)$_2$][Na]$_2$}2(NaCl) (10.0 g, 20.3 mmol) in water (40 g), under air. A yellow solid precipitated out which was washed with water (10 ml), with MeOH (10 ml) and dried under vacuum (6.2 g; yield=74%).

IR (neat): 2953.5 (m), 2950-2920 (w) 1568.1 (s); 1479 (s), 1406 (s).

$^1$H-NMR: 4.5 (m, 1H, CH); 4.3 (m, 1H, CH); 4.2 (m, 1H, CH); 4.0 (m, 1H, CH); 2.5 (m, 2H, CH$_2$); 2.3 (m, 2H, CH$_2$); 2.2 (m, 1H, CH$_2$); 2.1 (m, 1H, CH$_2$); 2.0 (m, 2H, CH$_2$); 1.12 (s, 9H, tBu); 1.11 (s, 9H, tBu).

$^{13}$C-NMR: 194.5 (O—C=O); 191.9 (O—C=O); 97.9 (CH); 96.5 (CH); 88.5 (CH); 83.5 (CH); 41.6 (C); 40.9 (C); 30.3 (CH$_2$); 29.8 (CH$_2$); 28.4 (CH$_2$); 28.2 (CH$_3$); 28.1 (CH$_2$); 27.9 (CH$_3$).

Synthesis of [(COD)Ru(O$_2$CCH$_3$)$_2$] by Direct Reaction of {[(COD)Ru(CO$_3$)$_2$][Na]$_2$}2(NaCl) with Acetic Acid in Water Under Nitrogen Acetic acid (5.1 g, 85.3 mmol) was slowly added at room temperature to a solution of {[(COD)Ru(CO$_3$)$_2$][Na]$_2$}2(NaCl) (10.0 g, 20.3 mmol) in water (40 g), under nitrogen. A solid precipitated which was collected washed with water (10 ml), cold MeOH (10 ml) and dried under vacuum to afford 4.9 g of product (yield=74%).

IR (neat): 3010-2800 (w); 1463 (s), 1395 (s).

$^1$H-NMR: 4.58 (m, 2H, CH); 3.2 (m, 2H, CH); 2.4 (m, 4H, CH$_2$); 2.2 (m, 2H, CH$_2$); 2.0 (2, 6H, CH$_3$ overlapped with m, 2H, CH$_2$).

$^{13}$C-NMR: 190.6 (O—C=O); 89.3 (CH); 84.6 (CH); 31.4 (CH$_2$); 27.0 (CH$_2$).

Synthesis of [(COD)Ru(O$_2$CPh)$_2$] by Direct Reaction of {[(COD)Ru(CO$_3$)$_2$][Na]$_2$}2(NaCl) with Acetic Acid in Water Under Nitrogen Benzoic acid (10.4 g, 85.3 mmol) was added portion wise at room temperature to a solution of {[(COD)Ru(CO$_3$)$_2$][Na]$_2$}2(NaCl) (10.0 g, 20.3 mmol) in water (40 g), under nitrogen. A solid precipitated which was collected washed with water (10 ml), cold MeOH (10 ml) and dried under vacuum to afford 7.1 g of product (yield=78%).

$^1$H-NMR: 8.1 (d, 4H, Ar); 7.6 (t, 2H, Ar); 7.4 (t, 4H, Ar); 4.8 (m, 2H, CH); 3.3 (m, 2H, CH); 2.5 (m, 4H, CH$_2$); 2.3 (m, 2H, CH$_2$); 2.1 (m, 2H, CH$_2$).

$^{13}$C-NMR: 185 (O—C=O); 131.8 (CH); 131.4 (C); 128.7 (CH); 128.6 (CH); 89.5 (CH); 85.0 (CH); 33.2 (CH$_2$); 28.0 (CH$_2$).

Synthesis of {[(COD)Ru(O$_2$CCl$_3$)$_2$]$_2$.(H$_2$O)} by Direct Reaction of Polymeric [(COD)RuCl$_2$]$_n$ with CCl$_3$COOH in Presence of a Base Under Nitrogen Trichloroacetic acid (16.0 g, 98 mmol) was added at room temperature to a solution of {[(COD)Ru(CO$_3$)$_2$][Na]$_2$}2(NaCl) (10.0 g, 20.3 mmol) in water (40 g), under nitrogen. A solid precipitated which was collected washed with water (10 ml), cold MeOH (10 ml) and dried under vacuum to afford 9.2 g of product (yield=85%).

IR (neat): 3151 (b) (H$_2$O); 3000-2800 (w) (COD); 1648 (s) (COO); 1347 (COO).

$^1$H-NMR: 13.1 (H$_2$O); 4.98 (m, 2H, CH); 4.75 (m, 4H, CH); 4.65 (m, 2H, CH); 2.7-2.0 (series of m, 16H, CH$_2$).

$^{13}$C-NMR: 175.3 (O—C=O); 174.0 (O—C=O); 99.8 (CH); 98.5 (CH); 95.0 (CH); 94.7 (overlapped CCl$_3$); 92.1 (CH); 87.5 (CH); 29.7 (CH$_2$); 29.3 (CH$_2$); 27.8 (CH$_2$); 27.7 (CH$_2$).

Synthesis of {[(COD)Ru(μ-O$_2$CEt)$_4$]}: by Reaction of [(COD)Ru(CO$_3$)$_2$][Cs]$_2$ with Propionic Acid Under Nitrogen Propionic acid (7.5 g, 101 mmol) was added at room temperature, under nitrogen atmosphere, to a suspension of [(COD)Ru(CO$_3$)$_2$][Cs]$_2$ (10.0 g, 16.9 mmol) in THF (50 ml). The reaction mixture was then heated to reflux and stirred under those conditions for 5 hours. It was then cooled down to room temperature and the precipitate was filtered off. The solution was evaporated to dryness and MeOH (30 ml) was added to give a crystalline solid which was collected by filtration and dried under vacuum (4.1 g, yield=68%).

$^1$H-NMR (CD$_2$Cl$_2$): 3.69 (broad s, 4H, CH); 2.58 (q, J=7.36 Hz, 4H, CH$_2$); 2.4 (m, 4H, CH$_2$); 2.16 (m, 4H, CH$_2$); 1.12 (t, J=7.36 Hz, 6H, CH$_3$).

$^{13}$C-NMR (CD$_2$Cl$_2$): 184.6 (O—C=O); 87.2 (CH); 33.57 (CH$_2$); 28.2 (CH$_2$); 9.8 (CH$_3$).

Synthesis of {[(COD)Ru(O$_2$CAd)]$_2$(μ-O$_2$CAd)$_2$}: by Direct Reaction of {[(COD)Ru(CO$_3$)$_2$][Na]$_2$}2 (NaCl) with 1-Adamantanecarboxylic Acid in Water Under Air 1-Adamantanecarboxylic acid (AdCOOH) (15.3 g, 85 mmol) was added at room temperature to a solution of {[(COD)Ru(CO$_3$)$_2$][Na]$_2$}2(NaCl) (10.0 g, 20.3 mmol) in water (50 g), under air. A yellow solid precipitated out which was washed with water (2×10 ml), with MeOH (2×5 mL) and dried under vacuum (10.6 g; 92%).

IR (neat): 2901 (s), 2848 (m) 1566 (s); 1392 (s).

$^1$H-NMR: 4.5 (m, 2H, CH); 4.3 (m, 2H, CH); 4.2 (m, 2H, CH); 4.0 (m, 2H, CH); 2.8-1.2 (series of m, 76H, CH+CH$_2$).

$^{13}$C-NMR: 193.4 (O—C=O); 190.9 (O—C=O); 97.8 (CH); 96.5 (CH); 88.3 (CH); 83.3 (CH); 43.7 (C); 42.9 (C); 40.4 (CH); 40.0 (CH); 37.4 (CH); 37.2 (CH); 30.3 (CH$_2$); 29.8 to (CH$_2$); 29.2 (CH$_2$); 28.9 (CH$_2$); 28.4 (CH$_2$); 28.2 (CH$_2$).

Synthesis of [(COD)Ru(O$_2$CPh(o-OMe))$_2$] by Reaction of {[(COD)Ru(CO$_3$)$_2$][Na]$_2$}2(NaCl) with o-Methoxy Benzoic Acid in Water o-Methoxy benzoic acid (12.9 g, 85 mmol) was added portion wise at room temperature to a solution of {[(COD)Ru(CO$_3$)$_2$][Na]$_2$}2(NaCl) (10.0 g, 20.3 mmol) in water (50 g), under nitrogen. A solid precipitated which was collected, washed with water (2×10 ml), cold MeOH (2×5 ml) and dried under vacuum to afford 7.9 g of product (76% yield).

$^1$H-NMR: 8.0 (m, 2H, Ar); 7.5 (m, 2H, Ar); 7.0 (m, 4H, Ar); 4.8 (m, 2H, CH); 3.9 (s, 3H, CH$_3$); 3.3 (m, 2H, CH); 2.4 (m, 4H, CH$_2$); 2.2 (m, 2H, CH$_2$); 2.1 (m, 2H, CH$_2$).

$^{13}$C-NMR: 184.5 (O—C=O); 160.2 (C); 134.3 (CH); 131.9 (CH); 122.5 (C); 120.3 (CH); 112.5 (CH); 90.1 (CH); 85.5 (CH); 56.3 (OCH$_3$); 31.9. (CH$_2$); 27.5 (CH$_2$).

Synthesis of [(COD)Ru(O$_2$C$^t$Bu)$_2$] by Reaction {[(COD)Ru(CO$_3$)]}.(DMF) with Pivalic Acid Pivalic acid (3.12 g, 30.6 mmol) was added at room temperature to a suspension of {[(COD)Ru(CO$_3$)]}.(DMF) (5 g, 14.6 mmol) in THF (30 ml). After overnight stirring, the reaction mixture was evaporated to dryness and cold MeOH was added to give [(COD)Ru(O$_2$CtBu)$_2$] which was collected, washed with cold MeOH and dried under vacuum (3.5 g, 58%).

IR (neat) ν: 2959 (m), 2950-2920 (w); 1476 (s), 1492(s), 1426 (s).

$^1$H-NMR: 4.5 (m, 2H, CH); 3.2 (m, 2H, CH); 2.38 (m, 2H, CH$_2$); 2.3 (m, 2H, CH$_2$); 2.2 (m, 2H, CH$_2$); 2.08 (s, 2H, CH$_2$); 1.05 (s, 18H, tBu).

$^{13}$C-NMR: 199 (O—C=O); 89.3 (CH); 85.7 (CH); 40.5 (C); 31.6. (CH$_2$); 27.7 (CH$_2$); 26.2 (CH$_3$).

Synthesis of [(COD)Ru(O$_2$CCH$_2$$^t$Bu)$_2$] by Reaction of {[(COD)Ru(CO$_3$)$_2$][Na]$_2$}2(NaCl) with t-Butylacetic Acid t-Butylacetic acid (9.4 g, 81.2 mmol) was slowly added at room temperature to a solution of {[(COD)Ru(CO$_3$)$_2$][Na]$_2$}2(NaCl) (10.0 g, 20.3 mmol) in water (40 g), under nitrogen. A yellow solid precipitated out which was washed with water (1×10 ml), with MeOH (2×5 ml) and dried under vacuum (6.9 g; 77%).

$^1$H-NMR: 4.5 (m, 2H, CH); 3.2 (m, 2H, CH); 2.38 (m, 2H, CH$_2$); 2.3 (m, 2H, CH$_2$); 2.2 (m, 2H, CH$_2$); 2.08 (s, 2H, CH$_2$); 2.0 (m, 2H, CH$_2$); 1.05 (s, 18H, tBu).

$^{13}$C-NMR: 192.8 (O—C=O); 89.3 (CH); 84.5 (CH); 51.6 (CH$_2$); 31.7. (CH$_2$); 31.2 (C); 29.9 (CH$_3$); 27.4. (CH$_2$).

What is claimed is:

1. A process for the preparation of a compound of formula (I)

{[(diene)Ru(OOCR$^1$)$_2$]$_n$(H$_2$O)$_v$}     (I)

wherein n is 1 or 2;
v is 0 or 1; and
R$^1$ represents:
a hydrogen atom;
a pyridyl group;
a phenyl group optionally substituted by one to five halogen atoms and/or C$_{1-4}$ alkyl or alkoxyl groups; or
a C$_{1-18}$ alkyl or alkenyl, optionally halogenated, and optionally substituted with one or two phenyl group, each phenyl group being optionally substituted by one to five halogen atoms and/or by C$_{1-4}$ alkyl or alkoxyl groups; and/or optionally substituted with one or two OH, or amino;
comprising the step of reacting a precursor compound of the formulae

[Ru(diene)(CO$_3$)$_2$]M$_n$     (II)

or

[Ru(diene)(CO$_3$)]     (II')

wherein "diene" is selected from the group consisting of COD (cycloocta-1,5-diene), NBD (norbornadiene), 2,4-dimethyl-1,3-pentadiene and cyclohepta-1,4-diene, M is an alkaline (n is 2) or alkaline earth (n is 1) cation;
in the presence of a carboxylic acid R$^1$COOH, wherein R$^1$ is as defined in formula (I).

2. A process according to claim 1, wherein the R$^1$ group represents:
a C$_{1-12}$ alkyl group, optionally halogenated, and optionally substituted with: one phenyl group optionally substituted by one to five halogen atoms and/or by C$_{1-4}$ alkyl or alkoxyl groups; and/or optionally substituted with one OH, or amino; or
a phenyl group optionally substituted by one to five halogen atoms and/or by C$_{1-4}$ alkyl or alkoxyl groups.

3. A process for the preparation of a compound of formula (I)

{[(diene)Ru(OOCR$^1$)$_2$]$_n$(H$_n$O)$_v$}     (I)

wherein n is 1 or 2;
v is 0 or 1;
"diene" represents a linear or branched $C_4$-$C_{15}$ hydrocarbon compound comprising two carbon-carbon double bonds or a cyclic $C_7$-$C_{20}$ hydrocarbon group comprising two carbon-carbon double bonds; and
$R^1$ represents:
a hydrogen atom;
a pyridyl group;
a phenyl group optionally substituted by one to five halogen atoms and/or $C_{1-4}$ alkyl or alkoxyl groups; or
a $C_{1-18}$ alkyl or alkenyl, optionally halogenated, and optionally substituted with one or two phenyl group, each phenyl group being optionally substituted by one to five halogen atoms and/or by $C_{1-4}$ alkyl or alkoxyl groups; and/or optionally substituted with one or two OH, or amino;
comprising the step of reacting a precursor compound of the formulae $$[Ru(diene)(CO_3)_2]M_n \quad \text{or} \qquad (II)$$

$$[Ru(diene)(CO_3)] \qquad (II')$$

wherein "diene" has the same meaning as defined in formula (I), M is an alkaline (n is 2) or alkaline earth (n is 1) cation; in the presence of a carboxylic acid $R^1COOH$, wherein $R^1$ is as defined in formula (I) wherein the $R^1$ group represents a $C_{2-10}$ alkyl group, optionally branched in the α and/or β position.

4. A process according to claim 1, wherein the $R^1$ group is a branched $C_{2-10}$ alkyl group comprising in the α position a tertiary or quaternary carbon atom and/or in the β position a quaternary carbon atom and said branched $C_{2-10}$ alkyl group being optionally substituted with one OH, or amino or one phenyl group, the phenyl group being optionally substituted by one to five halogen atoms and/or by $C_{1-4}$ alkyl or alkoxyl groups.

5. A process for the preparation of a compound of formula (I)

$$\{[(diene)Ru(OOCR^1)_2]_n(H_2O)_v\} \qquad (I)$$

wherein n is 1 or 2;
v is 0 or 1;
"diene" represents a linear or branched $C_4$-$C_{15}$ hydrocarbon compound comprising two carbon-carbon double bonds or a cyclic $C_7$-$C_{20}$ hydrocarbon group comprising two carbon-carbon double bonds; and
$R^1$ represents:
a hydrogen atom;
a pyridyl group;
a phenyl group optionally substituted by one to five halogen atoms and/or $C_{1-4}$ alkyl or alkoxyl groups; or
a $C_{1-18}$ alkyl or alkenyl, optionally halogenated, and optionally substituted with one or two phenyl group, each phenyl group being optionally substituted by one to five halogen atoms and/or by $C_{1-4}$ alkyl or alkoxyl groups; and/or optionally substituted with one or two OH, or amino;
comprising the step of reacting a precursor compound of the formulae $$[Ru(diene)(CO_3)_2]M_n \quad \text{or} \qquad (II)$$

$$[Ru(diene)(CO_3)] \qquad (II')$$

wherein the $R^1COOH$, and consequently the $R^1COO$ group of (I), is acetic, the mono-, di-, tri-chloroacetic, propionic, isobutyric, pivalic, $^tBu$-acetic, 2-Et-hexanoic, cyclohexanecarboxylic, picolinic, cinnaminic, benzoic, 4-Me-benzoic, 4-OMe-benzoic, 3,5-dichlorobenzoic, isovaleric, 1-adamantanecarboxylic or sec-butyric acid;
wherein "diene" has the same meaning as defined in formula (I), M is an alkaline (n is 2) or alkaline earth (n is 1) cation,
M is an alkaline (n is 2) or alkaline earth (n is 1) cation; and the reacting is conducted in the presence of a carboxylic acid $R^1COOH$, wherein $R^1$ is as defined in formula (I).

6. A compound of formula $$[Ru(diene)(CO_3)_2]M_n \quad \text{or} \qquad (II)$$

$$[Ru(diene)(CO_3)] \qquad (II')$$

wherein "diene" is selected from the group consisting of COD (cycloocta-1,5-diene), NBD (norbornadiene), 2,4-dimethyl-1,3-pentadiene and cyclohepta-1,4-diene M is an alkaline (n is 2) or alkaline earth (n is 1) cation.

7. A compound according to claim 6, wherein M represents a sodium, potassium, cesium, calcium, stronzium or barium cation.

8. A compound according to claim 6, selected from the group consisting of [Ru(COD)(CO$_3$)$_2$]Na$_2$; [Ru(COD)(CO$_3$)$_2$]K$_2$; [Ru(COD)(CO$_3$)$_2$]Cs$_2$; [Ru(NBD)(CO$_3$)$_2$]Na$_2$; [Ru(NBD)(CO$_3$)$_2$]K$_2$; [Ru(NBNCO$_3$)$_2$]Cs$_2$ and [Ru(COD)(CO$_3$)].

9. The process of claim 1 wherein each "diene" is the same.

10. The process of claim 3 wherein each "diene" is the same.

11. The process of claim 5 wherein each "diene" is the same.

12. The compound of claim 6 wherein each "diene" is the same.

* * * * *

UNITED STATES PATENT AND TRADEMARK OFFICE
CERTIFICATE OF CORRECTION

PATENT NO.       : 8,575,346 B2
APPLICATION NO.  : 13/698508
DATED            : November 5, 2013
INVENTOR(S)      : Bonomo et al.

It is certified that error appears in the above-identified patent and that said Letters Patent is hereby corrected as shown below:

Title Page:
Item 56, References Cited, Publications, the following changes are requested:

Albers et al. reference, second occurrence, please change "(β-aquobis(μ-trifluoroacetato)bis[(η$^4$-cycloocat-1,5-diene)(trifluoroacetato)ruthenium(II)]" to -- (μ-aquobis(μ-trifluoroacetato)bis[(η$^4$-cycloocat-1,5-diene)(trifluoroacetato)ruthenium(II)] --.

Demerseman et al. reference, change "[Ru(η$^6$-arene)(L)(MeCN)$_2$][BF$_4$]$_2$:" to -- [Ru(η$^6$-arene)(L)(MeCN)$_2$][BF$_4$]$_2$: --; and change "$_{H2}$O" to -- H$_2$O --.

In the Claims:

Column 12:
Line 39 (claim 6, line 8), change "cyclohepta-1,4-diene M" to -- cyclohepta-1,4-diene, M --.
Line 47 (claim 8, line 4), change "[Ru(NBNCO$_3$)$_2$]Cs$_2$" to -- [Ru(NBD)(CO$_3$)$_2$]Cs$_2$ --.

Signed and Sealed this
Thirty-first Day of December, 2013

Margaret A. Focarino
*Commissioner for Patents of the United States Patent and Trademark Office*